(12) United States Patent
Grasse et al.

(10) Patent No.: US 11,596,765 B2
(45) Date of Patent: Mar. 7, 2023

(54) MULTI-LUMEN MEDICAL DEVICES AND METHODS OF MANUFACTURING SAME

(71) Applicant: St. Jude Medical, Atrial Fibrillation Division, Inc., St. Paul, MN (US)

(72) Inventors: Martin Maitre Grasse, Minneapolis, MN (US); James V. Kauphusman, Champlin, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 1044 days.

(21) Appl. No.: 16/288,710

(22) Filed: Feb. 28, 2019

(65) Prior Publication Data

US 2019/0240447 A1 Aug. 8, 2019

Related U.S. Application Data

(60) Continuation of application No. 15/400,663, filed on Jan. 6, 2017, now Pat. No. 10,258,763, which is a
(Continued)

(51) Int. Cl.
*A61M 25/00* (2006.01)
*B29C 48/10* (2019.01)
(Continued)

(52) U.S. Cl.
CPC ..... *A61M 25/0012* (2013.01); *A61B 18/1492* (2013.01); *A61L 29/041* (2013.01); *A61M 25/005* (2013.01); *A61M 25/0026* (2013.01); *A61M 25/01* (2013.01); *A61M 25/0147* (2013.01); *B29C 48/0021* (2019.02); *B29C 48/022* (2019.02); *B29C 48/10* (2019.02); *B29C 48/21* (2019.02); *B29D 23/00* (2013.01);
(Continued)

(58) Field of Classification Search
CPC .... A61M 2025/0036; A61M 2025/004; A61M 25/0012; A61M 25/0026; A61M 25/005; A61M 25/0053; A61M 25/0147
See application file for complete search history.

(56) References Cited

U.S. PATENT DOCUMENTS 4,898,577 A 2/1990 Badger et al.
5,030,202 A 7/1991 Harris
(Continued)

*Primary Examiner* — Deanna K Hall
(74) *Attorney, Agent, or Firm* — Wiley Rein LLP

(57) ABSTRACT

A method of manufacturing a catheter shaft includes extruding an inner polymeric layer having a main lumen and two or more side lumens spaced about the main lumen; forming an outer polymeric layer about the inner polymeric layer; and inserting at least one elongate member, such as a wire, through each side lumen of the inner polymeric layer. The side lumens are less than about ⅕ the size of the main lumen. The method may further include the step of forming a braided layer between the inner polymeric layer and the outer polymeric layer. In an alternate embodiment, the method includes co-extruding an inner polymeric layer and a multi-lumen layer, the multi-lumen layer having two or more side lumens; forming an outer polymeric layer about the multi-lumen layer; and inserting at least one elongate member through each side lumen. Catheter assemblies made according to the described methods are also disclosed.

17 Claims, 7 Drawing Sheets

Related U.S. Application Data division of application No. 12/346,396, filed on Dec. 30, 2008, now abandoned.

(51) Int. Cl.

| | | |
|---|---|---|
| *B29C 48/21* | (2019.01) | |
| *B29C 48/00* | (2019.01) | |
| *A61B 18/14* | (2006.01) | |
| *A61L 29/04* | (2006.01) | |
| *A61M 25/01* | (2006.01) | |
| *F16L 11/22* | (2006.01) | |
| *B29D 23/00* | (2006.01) | |
| *A61B 18/18* | (2006.01) | |
| *B29C 49/04* | (2006.01) | |
| *B29K 27/18* | (2006.01) | |
| *B29L 31/00* | (2006.01) | |
| *A61B 18/00* | (2006.01) | |

(52) U.S. Cl.
CPC ............... *F16L 11/22* (2013.01); *A61B 18/18* (2013.01); *A61B 2018/00642* (2013.01); *A61B 2018/00839* (2013.01); *A61M 25/0053* (2013.01); *A61M 2025/004* (2013.01); *A61M 2025/0036* (2013.01); *B29C 49/04* (2013.01); *B29K 2027/18* (2013.01); *B29L 2031/7542* (2013.01)

(56) References Cited

U.S. PATENT DOCUMENTS

| | | | |
|---|---|---|---|
| 5,281,218 | A | 1/1994 | Imran |
| 5,327,889 | A | 7/1994 | Imran |
| 5,330,466 | A | 7/1994 | Imran |
| 5,348,554 | A | 9/1994 | Imran et al. |
| 5,368,564 | A | 11/1994 | Savage |
| 5,389,073 | A | 2/1995 | Imran |
| 5,391,147 | A | 2/1995 | Imran et al. |
| 5,478,330 | A | 12/1995 | Imran et al. |
| 5,527,279 | A | 6/1996 | Imran |
| 5,533,986 | A | 7/1996 | Mottola et al. |
| 5,554,136 | A | 9/1996 | Luther |
| 5,578,007 | A | 11/1996 | Imran |
| 5,755,760 | A | 5/1998 | Maguire et al. |
| 5,782,899 | A | 7/1998 | Imran |
| 5,823,955 | A | 10/1998 | Kuck et al. |
| 5,826,576 | A | 10/1998 | West |
| 5,882,346 | A | 3/1999 | Pomeranz et al. |
| 5,987,344 | A | 11/1999 | West |
| 6,026,316 | A | 2/2000 | Kucharczyk et al. |
| 6,066,125 | A | 5/2000 | Webster, Jr. |
| 6,119,041 | A | 9/2000 | Pomeranz et al. |
| 6,123,699 | A | 9/2000 | Webster, Jr. |
| 6,169,916 | B1 | 1/2001 | West |
| 6,183,463 | B1 | 2/2001 | Webster, Jr. |
| 6,210,362 | B1 | 4/2001 | Ponzi |
| 6,224,587 | B1 | 5/2001 | Gibson |
| 6,500,167 | B1 | 12/2002 | Webster, Jr. |
| 6,582,536 | B2 | 6/2003 | Shimada |
| 6,752,805 | B2 | 6/2004 | Maguire et al. |
| 6,837,867 | B2 | 1/2005 | Kortelling |
| 7,641,757 | B2 * | 1/2010 | Kampa ............ A61M 25/0138 156/308.2 |
| 7,706,891 | B2 | 4/2010 | Hastings et al. |
| 8,262,672 | B2 * | 9/2012 | Neidert ............ A61M 25/0023 600/585 |
| 2002/0040226 | A1 | 4/2002 | Laufer et al. |
| 2005/0149104 | A1 | 7/2005 | Leeflang et al. |
| 2006/0151923 | A1 | 7/2006 | Wilkowske et al. |
| 2007/0299424 | A1 | 12/2007 | Cumming et al. |
| 2008/0091169 | A1 | 4/2008 | Heideman et al. |
| 2008/0125699 | A1 | 5/2008 | Davis et al. |
| 2009/0062602 | A1 | 3/2009 | Rosenberg et al. |
| 2009/0166913 | A1 | 7/2009 | Guo et al. |
| 2009/0234283 | A1 | 9/2009 | Burton et al. |
| 2009/0287210 | A1 | 11/2009 | Kauphusman et al. |
| 2010/0168688 | A1 | 7/2010 | Santora et al. |
| 2012/0130217 | A1 | 5/2012 | Kauphusman et al. |
| 2014/0276043 | A1 | 9/2014 | Gupta |
| 2014/0336572 | A1 | 11/2014 | Heisel et al. |
| 2015/0306343 | A1 | 10/2015 | Dando et al. |
| 2015/0306805 | A1 | 10/2015 | Dando et al. |
| 2015/0306806 | A1 | 10/2015 | Dando et al. |

* cited by examiner

MULTI-LUMEN MEDICAL DEVICES AND METHODS OF MANUFACTURING SAME

CROSS-REFERENCE TO RELATED APPLICATIONS

This application is a continuation of U.S. application Ser. No. 15/400,663, filed 6 Jan. 2017, now pending, which is a division of U.S. application Ser. No. 12/346,396, filed 30 Dec. 2008, now abandoned, which are hereby incorporated by reference as though fully set forth herein.

BACKGROUND OF THE INVENTION a. Field of the Invention

The present invention pertains generally to electrophysiological devices having multiple lumens and methods for manufacturing multi-lumen electrophysiological devices. More particularly, the invention is directed to catheters and introducers and methods for manufacturing catheters and introducers having multiple, integrally-formed or co-extruded side lumens for enclosing elongate members, such as steering wires and electrical wires.

b. Background Art

Catheters are used for an ever-growing number of procedures. For example, catheters are used for diagnostic, therapeutic, and ablative procedures, to name just a few examples. Typically, the catheter is manipulated through a patient's vasculature and to the intended site, for example, a site within the patient's heart. The catheter typically carries one or more electrodes, which may be used for ablation, diagnosis, or the like.

Many catheters include one or more wires, for example, pull wires for steering and deflecting the catheter and/or electrical wires for energizing electrodes or other energy delivery or diagnostic elements. In some catheters, the wires are enclosed in small, polymeric liners or jackets that surround a main liner or jacket. The small jackets are manufactured separately from the main jacket and are subsequently glued along the length of the main jacket. The gluing process is time-consuming and can be inefficient. The small jackets must be glued substantially straight along the length of the main jacket; otherwise, steerable devices will not deflect properly. Also, the process becomes more time-consuming for devices using greater numbers of wires because greater numbers of small jackets must be glued along the length of the main jacket.

Accordingly, there is a growing need for improved catheters and improved methods for manufacturing catheters having liners or jackets that enclose the various wires to eliminate the time-consuming and inefficient gluing process.

BRIEF SUMMARY OF THE INVENTION

The present invention provides for medical devices and methods of manufacturing medical devices having multiple, integrally-formed side lumens enclosing elongate members, such as steering wires and electrical wires. The present invention also provides for medical devices and methods of manufacturing medical devices having a multi-lumen layer co-extruded with an inner layer.

An objective of the present invention is to provide methods of manufacturing a catheter assembly having multiple side lumens integrally-formed with a main lumen.

Another object of the invention is to provide methods of manufacturing a catheter assembly having an extruded polymer layer comprising a main lumen and multiple side lumens arranged about the main lumen.

Still another object of the present invention is to provide methods of manufacturing a catheter assembly having an inner polymeric layer co-extruded with a multi-lumen layer.

Yet another object of the present invention is to provide medical devices manufactured by the methods described herein.

A method of manufacturing a catheter assembly includes the steps of extruding an inner polymeric layer, the inner polymeric layer defining a main lumen having an inner surface and an outer surface and further defining two or more side lumens spaced about the outer surface of the main lumen. In one aspect, a size of the side lumens is less than about 1/5 to about 1/16 a size of the main lumen. The method further includes forming an outer polymeric layer disposed about the inner polymeric layer and inserting at least one elongate member through each side lumen of the inner polymeric layer. The elongate member may be a wire, such as a pull wire or an electrical wire.

The method may optionally include the step of forming a braided layer between the inner polymeric layer and the outer polymeric layer. The inner polymeric layer, the braided layer and the outer polymeric layer may be heated to bond the inner polymeric layer, the braided layer and the outer polymeric layers together. The inner polymeric layer may be made of polytetrafluoroethylene. The side lumens may be spaced symmetrically about the outer surface of the main lumen or may be spaced in any other orientation. In one aspect, the inner polymeric layer includes about 2-16 side lumens.

In another embodiment of the present invention, a method of manufacturing a catheter assembly includes co-extruding an inner polymeric layer and a multi-lumen layer. The inner polymeric layer includes an inner surface defining a main lumen and an outer surface, and the multi-lumen layer includes two or more side walls, each side wall defining a side lumen. The method further includes forming an outer polymeric layer about the multi-lumen layer and inserting at least one elongate member through each side lumen. The method may optionally include a step of forming a braided layer between the multi-lumen layer and the outer polymeric layer. The inner polymeric layer, the multi-lumen layer, the braided layer and the outer polymeric layer may also be heated to bond the layers together.

The inner polymeric layer and the multi-lumen layer may be made of the same or different materials. In one aspect, the inner polymeric layer and the multi-lumen layer are made of polytetrafluoroethylene. A size of the side lumens may be less than about 1/5 to about 1/16 a size of the main lumen. The multi-lumen layer may include about 2-16 side lumens, which may be spaced symmetrically about the outer surface of the main lumen, or in any other orientation. The elongate member may be a wire, such as a pull wire or an electrical wire.

In yet another aspect of the present invention, a catheter assembly includes an inner extruded polymeric layer and an outer polymeric layer disposed about the inner extruded polymeric layer. The inner extruded polymeric layer includes a main lumen having an inner surface and an outer surface and two or more side lumens spaced about the outer surface of the main lumen. The device further includes at least one elongate member extending through one of the side lumens. In one embodiment, a braided layer may be disposed between the inner extruded polymeric layer and the outer polymeric layer. In one aspect, a size of the side lumens may be less than about ⅕ to about ¹⁄₁₆ a size of the main lumen. The side lumens may be spaced symmetrically about the outer surface of the main lumen, or in a non-symmetrical orientation. The inner extruded polymeric layer may include about 2-16 side lumens. The inner extruded polymeric layer may be made of polytetrafluoroethylene. In one embodiment, the elongate member may be a wire, such as a pull wire or an electrical wire.

In still another aspect of the present invention, a catheter assembly includes an inner polymeric layer having an inner surface defining a main lumen and having an outer surface and a multi-lumen layer disposed about the outer surface of the inner polymeric layer. The multi-lumen layer includes two or more side walls, each side wall defining a side lumen. The multi-lumen layer and the inner polymeric layer are co-extruded. The catheter shaft further includes an outer polymeric layer disposed about the multi-lumen layer and at least one elongate member extending through one of the side lumens. In one embodiment, a braided layer may be disposed between the multi-lumen layer and the outer polymeric layer. A size of the side lumens may be less than about ⅕ to about ¹⁄₁₆ a size of the main lumen. The multi-lumen layer may include about 2-16 side lumens. The side lumens may spaced symmetrically about the outer surface of the main lumen or in a non-symmetrical orientation. In one embodiment, the elongate member may be a wire, such as a pull wire or an electrical wire.

An advantage of providing medical devices having multiple, integrally-formed lumens for enclosing elongate members is a shorter manufacturing process.

Another advantage of providing medical devices having multiple, integrally-formed lumens for carrying elongate members is a more efficient manufacturing process and fewer product defects.

The foregoing and other aspects, features, details, utilities, and advantages of the present invention will be apparent from reading the following description and claims, and from reviewing the accompanying drawings.

DETAILED DESCRIPTION OF THE INVENTION

Disclosed herein are medical devices and methods of manufacturing medical devices, for example catheters and introducers, having multiple side lumens integrally-formed or co-extruded with a main lumen. The side lumens enclose elongate members, for example steering wires and electrical wires. The present invention provides catheters and methods of manufacturing catheters suitable for use in the human vasculature for known medical procedures, such as cardiac diagnostic and therapeutic procedures including, without limitation, electrophysiological mapping and cardiac ablation. It is contemplated, however, that the described features may be incorporated into any number of catheters or other devices, such as steerable introducers, as would be appreciated by one of ordinary skill in the art.

Figure 1:
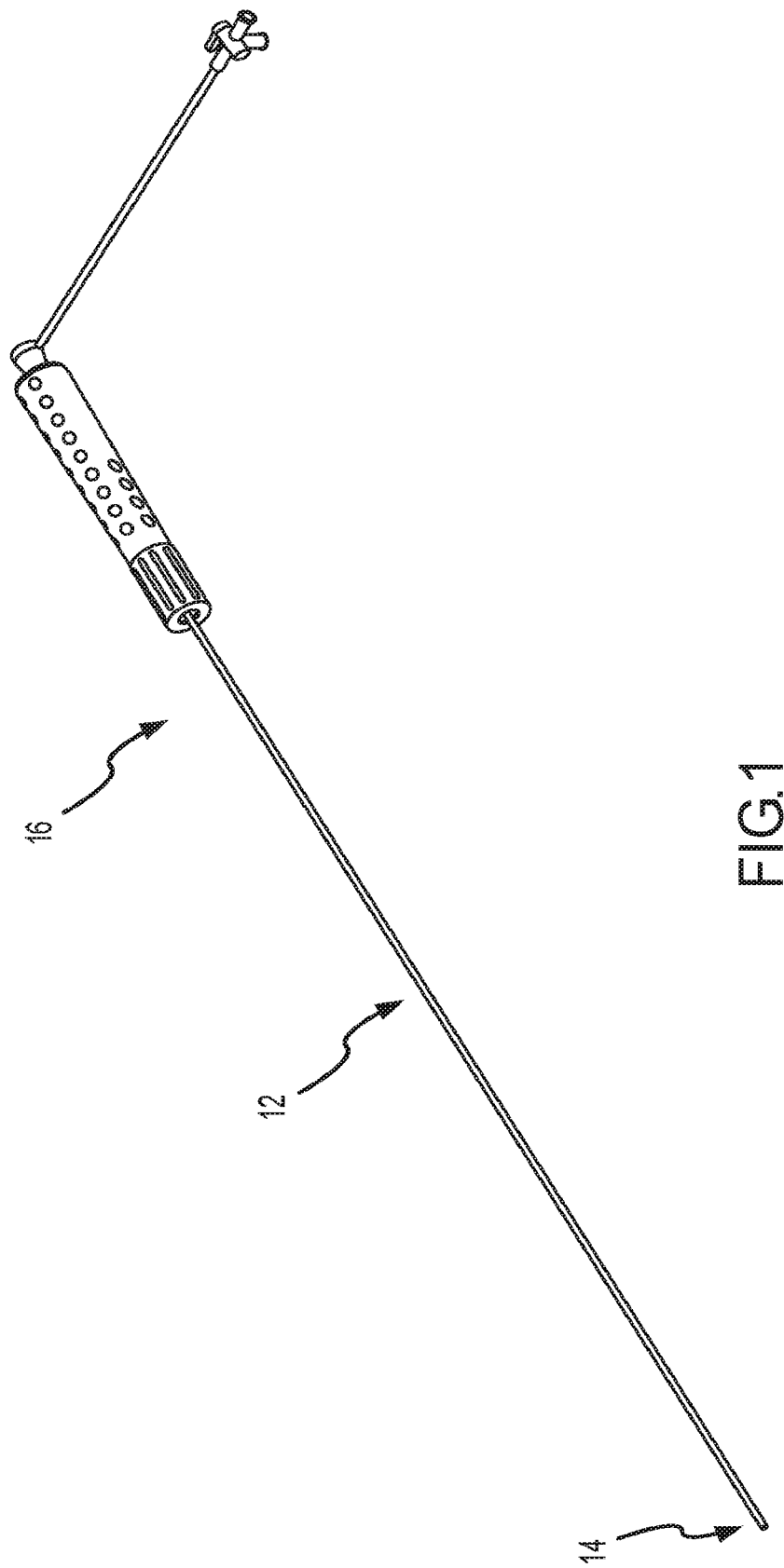
FIG. 1 is a perspective view of a catheter according to an embodiment of the present invention.

FIG. 1 is a perspective view of one embodiment of a catheter 12 of the present invention. Catheter 12 has a proximal portion 16 and a distal portion 14.

One method of manufacturing a catheter 12 according to the present invention will be described with reference to FIGS. 3-5. As they are assembled, the catheter components will be collectively referred to as a catheter assembly.

Figure 3:
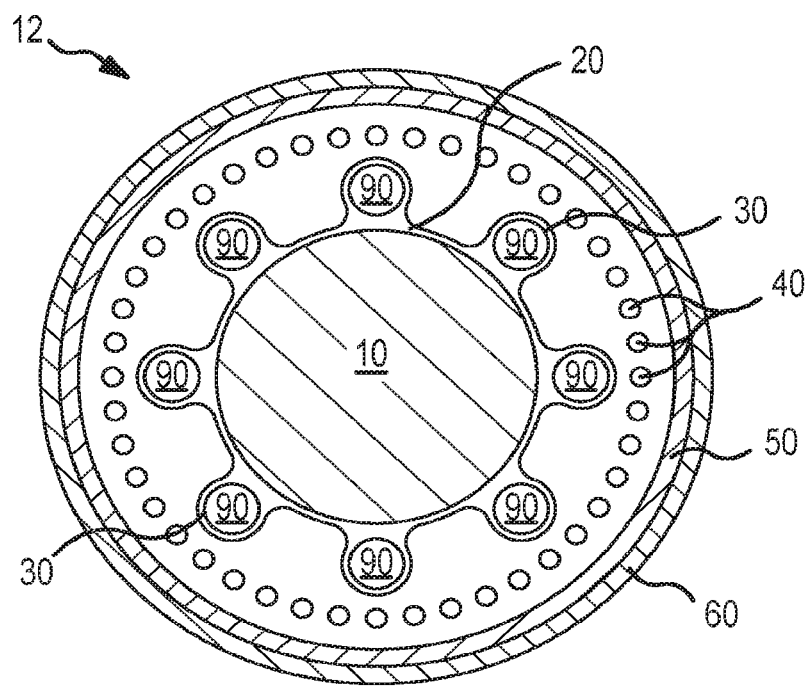
FIG. 3 is a cross-sectional view of a catheter assembly having an inner layer as depicted in FIG. 2A, prior to the application of heat to melt process the outer layer.

FIG. 3 displays a cross-section of a catheter assembly 12 prior to melt-processing of the layers by heating. A mandrel 10 may be the first component during manufacture of the catheter assembly 12. The mandrel 10 may be round in cross-section and may be from about 6 inches to about 4 feet in length. The mandrel 10 has a distal end and a proximal end. A first or inner polymeric layer 20 is placed on mandrel 10. Inner polymeric layer 20 may be knotted at one end (e.g. the distal end) and then fed onto mandrel 10.

Several embodiments of the inner polymeric layer 20 are depicted in FIGS. 2A-D. In general, the inner polymeric layer 20 includes a main lumen 11 having an inner surface 13 and an outer surface 15. The inner polymeric layer 20 further includes multiple integrally-formed side lumens 30 spaced about the outer surface 15 of the main lumen 11. As a person of skill in the art will understand, however, the integrally-formed side lumens 30 may alternatively be spaced about the inner surface 13 of the main lumen 11. The side lumens 30 may be spaced symmetrically about the main lumen 11 (see, for example, FIG. 2A), but need not be in a symmetrical orientation (see, for example, FIG. 2C).

The inner polymeric layer 20 is an extruded polymer. In one embodiment, the inner polymeric layer 20 is an extruded polytetrafluoroethylene (PTFE) tubing, such as Teflon® brand tubing, which is available commercially. The inner polymeric layer 20 may optionally be chemically etched to provide better adhesion during melt processing. As a person of skill in the art will appreciate, the inner polymeric layer 20 may be extruded from other melt processable polymers, including, without limitation, polyetheretherketone (PEEK), polyimides, polyesters, polyamides, polysulfones, polyketones, other fluoropolymers, and the like. In one aspect, the inner polymeric layer 20 uses PTFE as a coating over another polymer material, for example, a polyimide extrusion lined with PTFE. In another aspect, the inner polymeric layer 20 is made of a material with a melting temperature higher than that of an outer layer 50, which will be further described below, such that the inner polymeric layer 20 will withstand melt processing of the outer layer 50.

Figure 2A:
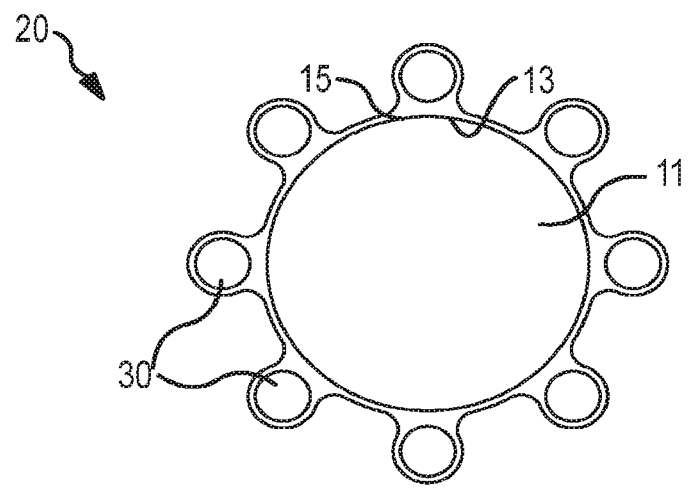
FIGS. 2A-D depict cross-sectional views of various embodiments of an inner layer of a catheter assembly according to the invention.
Figure 2B:
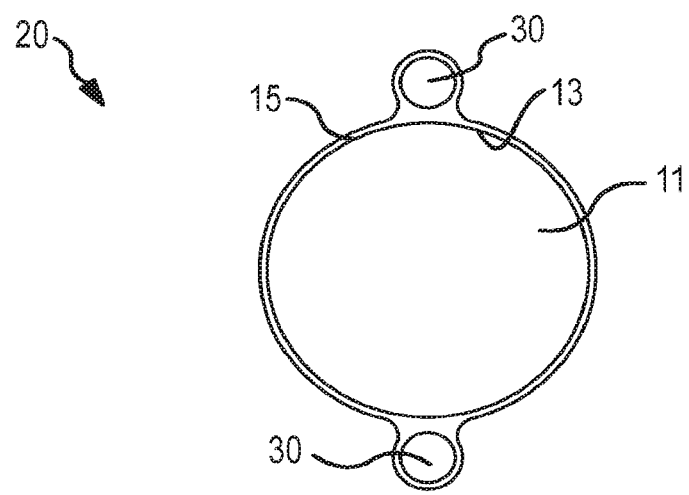
Figure 2C:
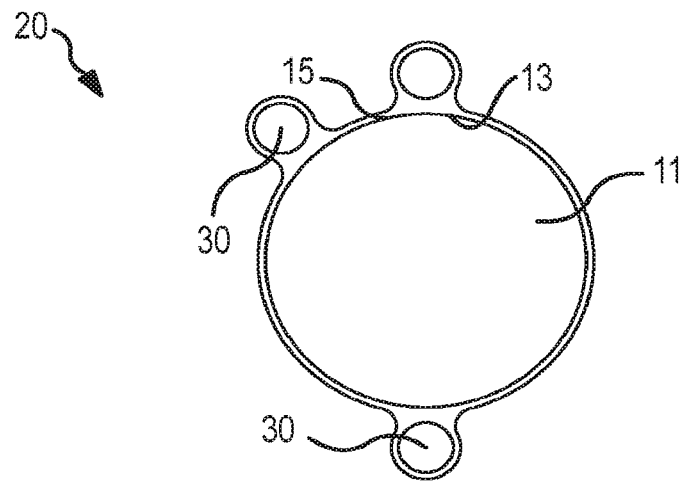
Figure 2D:
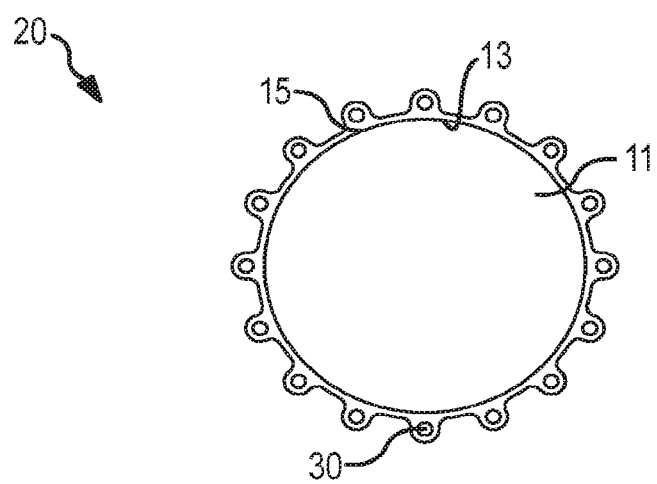

In one aspect, the side lumens 30 are about ⅕ the size of the main lumen 11 (see, for example, FIGS. 2A-C). In another aspect, the side lumens 30 may be about ¹⁄₁₆ the size of the main lumen 11 or smaller (see, for example, FIG. 2D). The side lumens 30 are sized to conformably enclose at least one elongate member, for example a pull wire or an electrical wire, while facilitating at least some movement of the elongate member within the side lumen 30 and at the same time minimizing friction caused by movement of the elongate member within the side lumen 30. A person of skill in the art will appreciate that the side lumens 30 can be sized and shaped to accommodate elongate member of various dimensions and cross-sectional configurations. The side lumens 30 need not have the same shape as the cross-section of the elongate members that they encase. The side lumens 30 may be round, oval, rectangular, or another like shape.

As shown in FIG. 2B, inner polymeric layer 20 may include two side lumens 30. The side lumens 30 may be spaced in an opposing orientation as shown in FIG. 2B, or may be spaced in any other orientation about the circumference of the main lumen 11. For example, the side lumens 30 may be immediately adjacent one another or may be spaced about the circumference of the main lumen 11 by about 45 degrees, by about 90 degrees or more. In another aspect, the inner polymeric layer 20 includes more than two side lumens 30. For example, the inner polymeric layer 20 may include up to 8 side lumens, up to 16 side lumens or more than 16 side lumens (see, for example, FIGS. 2A-D). As a person of skill in the art will understand, the inner polymeric layer 20 can be modified to accommodate various numbers of elongate members having various dimensions and cross-sectional configurations.

As further shown in FIGS. 2A-2D, in one aspect, the inner polymeric layer 20 has a scalloped or ribbed profile. This structure is particularly advantageous for steerable devices because it provides greater flexibility. The amount of space between adjacent side lumens 30 may vary depending on the number of side lumens present and the location of the side lumens about the main lumen 11.

Referring again to FIG. 3, the extruded inner polymeric layer 20 is placed on the mandrel 10. A small diameter mandrel or set-up wire 90 may be placed within the side lumens 30 to maintain the integrity of the side lumens during processing. Alternatively, a pull wire may be inserted through one or more of the side lumens 30 in lieu of a small diameter mandrel 90. In still other embodiments, the side lumens 30 may be maintained during processing via the use of a pressurized fluid as described in U.S. patent publication no. US 2006/0151923, which is incorporated herein by reference in its entirety.

An outer polymeric layer 50 is then placed over the inner polymeric layer 20. The outer polymeric layer 50 may be made of either single or multiple sections of tubing that may be either butted together or overlapped with each other. In one aspect, the outer polymeric layer 50 is made of a melt-processable polymer, such as polyether block amides, nylon, polyethylene and other thermoplastic elastomers. For example, the outer polymeric layer 50 may be made of Pebax®, polyether block amide made by Arkema, Inc. Pebax® of various durometers may be used, including, without limitation, Pebax 20D to Pebax 72D. The outer polymeric layer 50 may also comprise more than one layer or segment, including for example two or more tubes of a melt processing polymer arranged to abut one another and/or to overlap one another.

Optionally, a braided layer 40 may be placed over the inner polymeric layer 20 before the outer polymeric layer 50 is applied. The braided layer 40 may be formed of stainless steel wire, including, for example, 0.003" high tensile stainless steel wire. The braided layer 40 may also be formed of a metal alloy, for example, a copper alloy. The braided layer 40 may be formed in a standard braid pattern and density, for example, about 16 wires at about 45 to about 60 picks per inch ("PPI") density. Alternatively, a braid may be used that is characterized by a varying braid density. For example, the braided layer 40 may be characterized by a first braid density at the proximal end 16 of the catheter 12 and then transition to one or more different braid densities as the braided layer 40 approaches the distal end 14 of the catheter 12. The braid density at the distal end 14 may be greater or less than the braid density at the proximal end 16. A catheter assembly having a braided layer with a varying braid density in described in U.S. patent publication no. 2007/0299424, which is incorporated herein by reference in its entirety. In a specific example, the braid density at the base (i.e., proximal end 16) is about 50 PPI and the braid density at distal end 14 is about 10 PPI. In another embodiment, the braid density at distal end 14 is about 20% to about 35% of the braid density at the base/proximal end 16.

The braided layer 40 may be formed separately on a disposable core. One or more portions of the braided layer 40 may be heat tempered and cooled before incorporation into the catheter assembly 12 by methods that are known to those of ordinary skill in the art. The action of heat tempering may help to release the stress on the wire and help reduce radial forces. Alternatively, the braided layer 40 may be braided directly about the inner layer 20. A layer of heat shrink 60 may optionally be placed over the top of the outer layer 50. The heat shrink layer 60 may comprise a fluoropolymer or polyolefin material.

Figure 4:
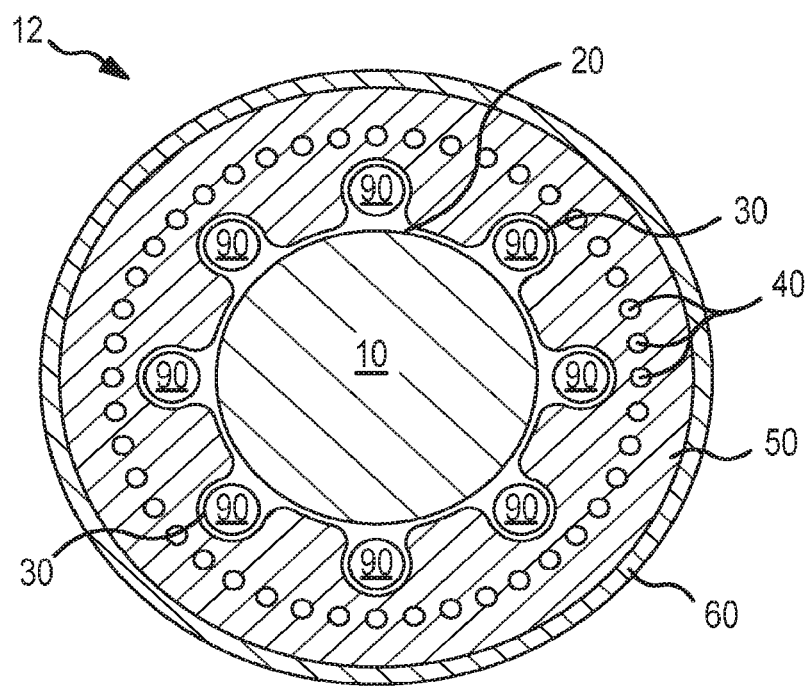
FIG. 4 depicts a cross-sectional view of a catheter assembly having an inner layer as depicted in FIG. 2A, after the application of heat to melt process the outer layer.

FIG. 4 depicts the catheter assembly 12 after a lamination process. The catheter assembly 12 may be laminated by heating the catheter assembly until the material comprising the outer layer 50 flows and redistributes within the catheter assembly 12. The heat shrink layer 60 has a higher melting temperature than the outer layer 50; therefore, during the melt process, the heat shrink layer 60 retains its tubular shape and forces the liquefied outer layer 50 material to redistribute throughout braided layer 40 (if present) and into the spaces between adjacent side lumens 30 of inner polymeric layer 20. The catheter assembly 12 may then be cooled. In FIG. 4, the mandrel 10 is still in place.

Figure 5:
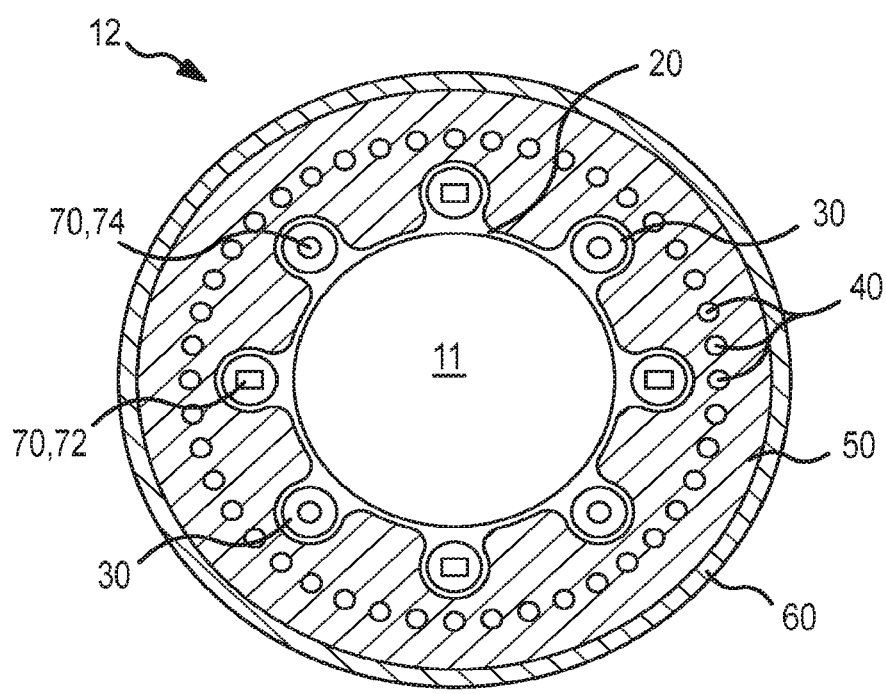
FIG. 5 is a cross-sectional view of a catheter assembly having multiple integrally-formed side lumens with pull wires and electrical wires extending through the side lumens.

The mandrel 10 may be removed from catheter assembly 12, leaving behind a lumen 11 as illustrated in FIG. 5, which depicts a catheter 12 made in accordance with the method of the present invention subsequent to the application of heat for the lamination process. If used, the small diameter mandrels (or set-up wires) 90 may also be removed from the side lumens 30.

At least one elongate member 70 may be inserted through the side lumens 30. The elongate members 70 may be used for a variety of purposes, for example to provide steerability or deflectability or to conduct energy to energy delivery elements, including, for example, electrodes, ultrasound transducers or microwave elements. The elongate members 70 may comprise a wide range of materials, including, but not limited to, a metallic material, such as a metallic wire, alloy or clad material, a polymer material, including conductive polymers, a composite material, a fibrous material, such as high strength synthetic fibers made of high performance engineering polymer materials (e.g., Kevlar® fibers and the like), a resilient member, and a thread.

As one example, a flat pull wire may be used in accordance with the present invention. The flat pull wire may be made of stainless steel and is may be from about 0.002-0.008 inches by about 0.006-0.024 inches, or larger. An example of a pull wire that is suitable for use with the present invention is described in U.S. patent publication no. 2007/0299424, which has been incorporated herein by reference in its entirety. A person of skill in the art will appreciate, however, that other types of pull wires may be used with the present invention, including, for example, pull wires having circular or oval cross sections and pull wires made of clad metals or metal alloys. In addition, the pull wire 72 may also serve as the electrical wire 74, or separate electrical wires may be used.

Optionally, the heat shrink layer 60 may be left in place around the outer layer 50, as depicted in FIG. 5, even after the mandrel 10 is removed. If the heat shrink 60 is removed, the outer layer 50 becomes the outermost layer of the catheter 12. The result is a substantially circular catheter 12 with multiple side lumens 30 integrally-formed within inner layer 20, each side lumen containing at least one elongate member 70.

Catheter 12 may further include one or more pull rings (not shown) to provide steerability. The pull wires are mechanically coupled to the one or more pull rings according to known methods.

Figure 6:
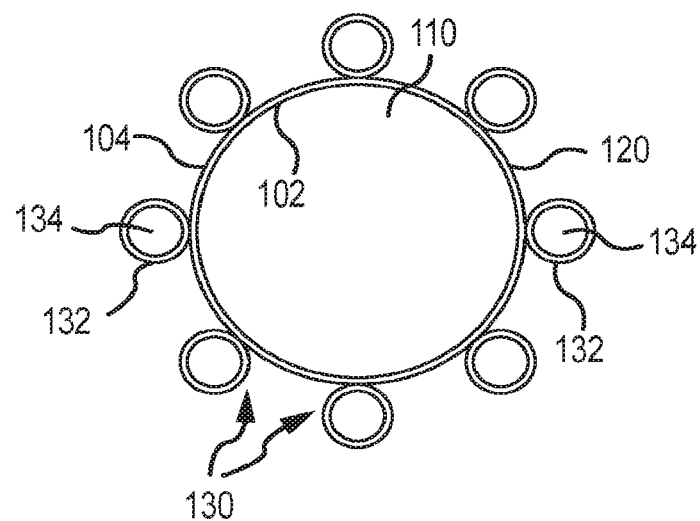
FIG. 6 depicts a cross-sectional view of an inner layer of a catheter assembly according to another embodiment of the present invention.

Another method of manufacturing the catheter 12 according to the present invention will be described with reference to FIGS. 6-9. In this embodiment, an inner polymeric layer 120 and a multi-lumen layer 130 are co-extruded. FIG. 6 depicts the inner polymeric layer 120 after co-extrusion with the multi-lumen layer 130. The inner polymeric layer 120 includes an inner surface 102 defining a main lumen 110 and an outer surface 104. The multi-lumen layer 130 includes two or more side walls 132 and each side wall 132 defines a side lumen 134. In one embodiment, the side walls 132 are spaced about the outer surface 104 of the inner polymeric layer 120. In an alternate embodiment, the side walls 132 are spaced about the inner surface 102 of the inner polymeric layer 120. The side walls 132 may be spaced symmetrically about the outer surface 104 of the inner polymeric layer 120, but need not be in a symmetrical orientation.

The features of the side lumens 30 described above with reference to FIGS. 2A-2D, including the number, dimensions, shapes and orientation of the side lumens about the outer surface 15 of the main lumen 11 apply equally to the side lumens 134 comprising multi-lumen layer 130. Thus, the number, dimensions, shapes and orientation of the side lumens 134 in the multi-lumen layer can be selected by a person of ordinary skill to accommodate multiple elongate members of various sizes and cross-sectional configurations.

The inner polymeric layer 120 and the multi-lumen layer 130 may be made of the same or different materials. In one embodiment, the inner polymeric layer 120 and the multi-lumen layer 130 are extruded polytetrafluoroethylene (PTFE) tubing, such as Teflon® brand tubing, which is available commercially. The inner polymeric layer 120 may optionally be chemically etched to provide better adhesion during melt processing. As a person of skill in the art will appreciate, the inner polymeric layer 120 may be made of other melt processable polymers. In one aspect, the inner polymeric layer 120 is made of a material with a melting temperature higher than that of an outer layer 160, which will be further described below, such that the inner polymeric layer 120 will withstand melt processing of the outer layer 160.

Figure 7:
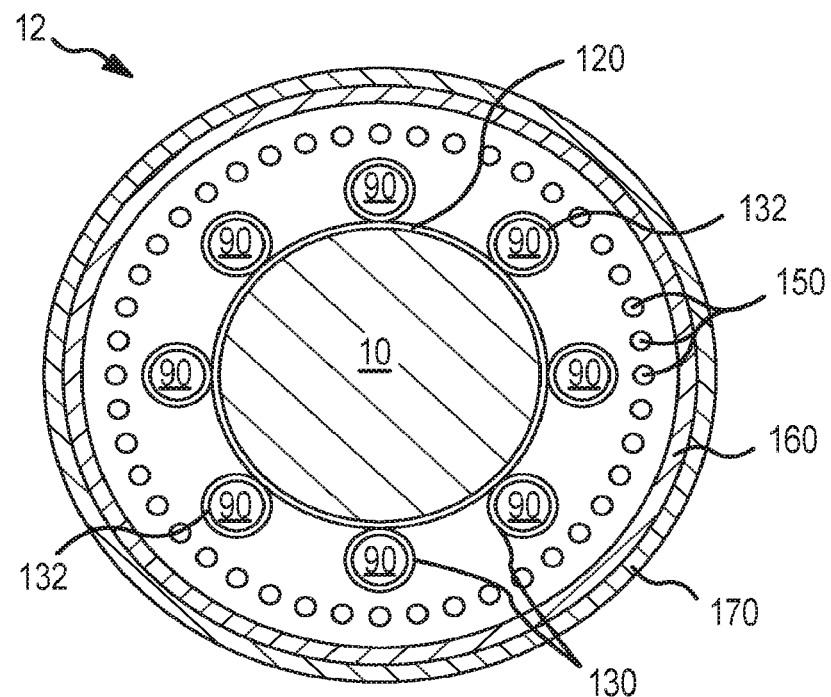
FIG. 7 illustrates a cross-sectional view of a catheter assembly having a multi-lumen layer as depicted in FIG. 6, prior to the application of heat to melt process the outer layer.

FIG. 7 displays a cross-section of a catheter assembly prior to melt-processing of the layers by heating. The inner polymeric layer 120 and multi-lumen layer 130 are co-extruded. The co-extruded layers are placed on mandrel 10. A small diameter mandrel or set-up wire 90 may be placed within the side lumens 134 to maintain the integrity of the side lumens during processing. Alternatively, a pull wire (FIG. 9) may be inserted through one or more of the side lumens 132 in lieu of a small diameter mandrel 90. In still other embodiments, the side lumens 132 may be maintained during processing via the use of a pressurized fluid.

An outer polymeric layer 160 is then placed over the multi-lumen layer 130. The outer polymeric layer 160 may be made of either single or multiple sections of tubing that may be either butted together or overlapped with each other. In one aspect, the outer polymeric layer 160 is made of a melt-processable polymer, such as polyether block amides, nylon, polyethylene and other thermoplastic elastomers. For example, the outer polymeric layer 160 may be made of Pebax®, polyether block amide made by Arkema, Inc. Pebax® of various durometers may be used, including, without limitation, Pebax 20D to Pebax 72D. The outer polymeric layer 160 may also comprise more than one layer or segment, including for example two or more tubes of a melt processing polymer arranged to abut one another and/or to overlap one another.

Optionally, a braided layer 150 may be placed over the multi-lumen layer 130 before the outer polymeric layer 160 is applied. The braided layer 150 may have any of the characteristics described above with reference to the braided layer 40 (FIG. 3). The braided layer 150 may be formed separately on a disposable core. One or more portions of the braided layer 150 may be heat tempered and cooled before incorporation into the catheter assembly by methods that are known to those of ordinary skill in the art. The action of heat tempering may help to release the stress on the wire and help reduce radial forces. A layer of heat shrink 170 may optionally be placed over the top of the outer layer 160. The heat shrink layer 170 may comprise a fluoropolymer or polyolefin material.

Figure 8:
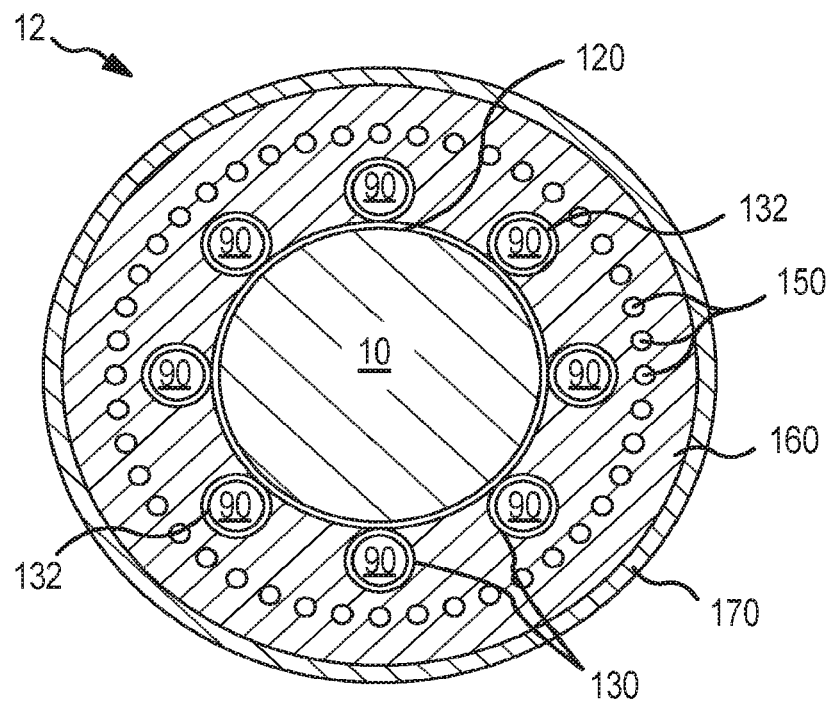
FIG. 8 is a cross-sectional view of a catheter assembly having a multi-lumen layer as depicted in FIG. 6, after the application of heat to melt process the outer layer.

FIG. 8 depicts the catheter assembly after a lamination process. The catheter assembly may be laminated by heating the catheter assembly until the material comprising the outer layer 160 flows and redistributes within the catheter assembly. The heat shrink layer 170 has a higher melting temperature than the outer layer 160; therefore, during the melt process, the heat shrink layer 170 retains its tubular shape and forces the liquefied outer layer 160 material to redistribute throughout braided layer 150 (if present) and around the side lumens 134 of the multi-lumen layer 130. The catheter assembly may then be cooled. In FIG. 8, the mandrel 10 is still in place.

Figure 9:
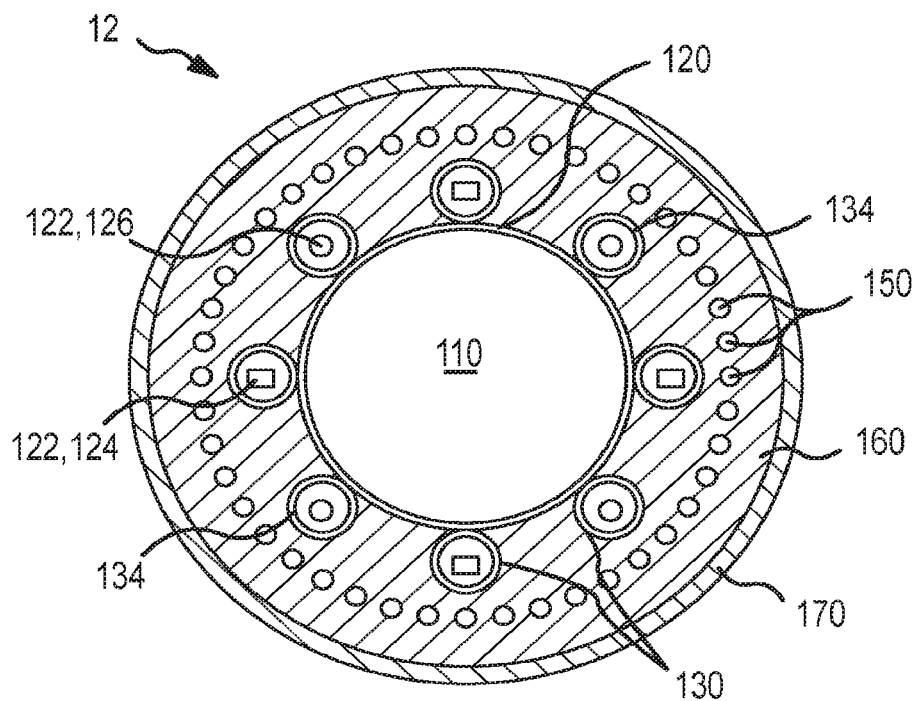
FIG. 9 depicts is a cross-sectional view of a catheter assembly having a co-extruded multi-lumen layer with pull wires and electrical wires extending through the side lumens of the multi-lumen layer.

The mandrel 10 may be removed from catheter assembly 12, leaving behind a lumen 110 as illustrated in FIG. 9, which depicts a catheter 12 made in accordance with the method of the present invention subsequent to the application of heat for the lamination process. If used, the small diameter mandrels (or set-up wires) 90 may also be removed from the side lumens 134 and at least one elongate member 122, such as a pull wire 124 or electrical wire 126, may be inserted through the side lumens 134.

Optionally, the heat shrink layer 170 may be left in place around the outer layer 160, as depicted in FIG. 9, even after the mandrel 10 is removed. If the heat shrink 170 is removed, the outer layer 160 becomes the outermost layer of the catheter 12. The result is a substantially circular catheter 12 with multiple side lumens 134 co-extruded with inner polymeric layer 120, each side lumen containing at least one elongate member 122.

Although multiple embodiments of this invention have been described above with a certain degree of particularity, those skilled in the art could make numerous alterations to the disclosed embodiments without departing from the spirit or scope of this invention. For example, person of skill in the art could modify inner polymeric layer 20 and multi-lumen layer 130 to accommodate numerous combinations of pull wires and electrical wires of various shapes and dimensions by modifying the number, size and orientation of the side lumens 30, 134 within these layers.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter assembly formed according to a process comprising:
    co-extruding an inner polymeric layer of a first polymeric material and a multi-lumen layer of a second polymeric material different from the first polymeric material, wherein the inner polymeric layer defines a main lumen and the multi-lumen layer defines two or more side lumens spaced about the main lumen, and wherein a size of the two or more side lumens is less than a size of the main lumen;
    forming an outer polymeric layer about the co-extruded inner polymeric layer and multi-lumen layer; and
    inserting at least one elongate member through each of the two or more side lumens.

2. The catheter assembly according to claim 1, wherein the two or more side lumens are spaced symmetrically about the main lumen.

3. The catheter assembly according to claim 1, wherein the multi-lumen layer defines between two and sixteen side lumens.

4. The catheter assembly according to claim 3, wherein the multi-lumen layer defines between six and sixteen side lumens.

5. The catheter assembly according to claim 1, wherein the size of the two or more side lumens is between $\frac{1}{5}$ and $\frac{1}{16}$ the size of the main lumen.

6. The catheter assembly according to claim 1, wherein the first polymeric material comprises polytetrafluoroethylene.

7. The catheter assembly according to claim 1, wherein the process further comprises forming a braided layer between the outer polymeric layer on one side and the co-extruded inner polymeric layer and multi-lumen layer on another side.

8. The catheter assembly according to claim 1, wherein the process further comprises heating the co-extruded inner polymeric layer and multi-lumen layer and the outer polymeric layer to bond the co-extruded inner polymer layer and multi-lumen layer to the outer polymeric layer.

9. The catheter assembly according to claim 1, wherein the at least one elongate member comprises at least one of a pull wire and an electrical wire.

10. A catheter assembly, comprising:
    a co-extrusion of an inner polymeric layer of a first polymeric material that defines a main lumen and a multi-lumen layer of a second polymeric material different from the first polymeric material that defines two or more side lumens spaced about the main lumen, wherein a size of the two or more side lumens is less than a size of the main lumen;
    an outer polymeric layer disposed about the co-extrusion of the inner polymeric layer and the multi-lumen layer; and
    at least one elongate member extending through each of the two or more side lumens.

11. The catheter assembly according to claim 10, wherein the two or more side lumens are spaced symmetrically about the main lumen.

12. The catheter assembly according to claim 10, wherein the multi-lumen layer defines between two and sixteen side lumens.

13. The catheter assembly according to claim 12, wherein the multi-lumen layer defines between six and sixteen side lumens.

14. The catheter assembly according to claim 10, wherein the size of the two or more side lumens is between $\frac{1}{5}$ and $\frac{1}{16}$ the size of the main lumen.

15. The catheter assembly according to claim 10, wherein the first polymeric material comprises polytetrafluoroethylene.

16. The catheter assembly according to claim 10, further comprising a braided layer disposed between the outer polymeric layer on one side and the co-extrusion of the inner polymeric layer and the multi-lumen layer on another side.

17. The catheter assembly according to claim 10, wherein the at least one elongate member comprises at least one of a pull wire and an electrical wire.

* * * * *